United States Patent
Bray et al.

(10) Patent No.: US 10,822,626 B2
(45) Date of Patent: Nov. 3, 2020

(54) SELECTIVE EXTRACTION OF BOTANICALS FROM PLANT MATERIAL

(71) Applicant: Azoth Solutions, LLC, Denver, CO (US)

(72) Inventors: Sheldon Bray, Seattle, WA (US); Jon Aaron Bray, Seattle, WA (US)

(73) Assignee: Azorth Solutions, LLC, Denver, CO (US)

( * ) Notice: Subject to any disclaimer, the term of this patent is extended or adjusted under 35 U.S.C. 154(b) by 0 days.

(21) Appl. No.: 16/194,129

(22) Filed: Nov. 16, 2018

(65) Prior Publication Data

US 2019/0153484 A1    May 23, 2019

Related U.S. Application Data

(60) Provisional application No. 62/588,108, filed on Nov. 17, 2017.

(51) Int. Cl.
| | |
|---|---|
| *A61K 36/185* | (2006.01) |
| *C12P 7/22* | (2006.01) |
| *C07D 311/80* | (2006.01) |
| *A61K 31/352* | (2006.01) |

(52) U.S. Cl.
CPC ........... *C12P 7/22* (2013.01); *A61K 31/352* (2013.01); *A61K 36/185* (2013.01); *C07D 311/80* (2013.01); *A61K 2236/333* (2013.01); *A61K 2236/39* (2013.01)

(58) Field of Classification Search
None
See application file for complete search history.

(56) References Cited

U.S. PATENT DOCUMENTS

| | | | |
|---|---|---|---|
| 3,944,189 A | 3/1976 | Singleton | |
| 4,059,922 A | 11/1977 | DiGiancinto | |
| 4,075,785 A | 2/1978 | Jones | |
| 4,218,847 A | 8/1980 | Leroux | |
| 4,704,818 A | 11/1987 | Cameron | |
| 4,869,019 A | 9/1989 | Ehrlich | |
| 4,965,962 A | 10/1990 | Akagi | |
| 5,136,804 A | 8/1992 | Rothem | |
| 6,000,173 A | 12/1999 | Schow | |
| 6,021,602 A | 2/2000 | Orsi | |
| 7,823,328 B2 | 11/2010 | Walhovd | |
| D638,743 S | 5/2011 | Bouchard | |
| 8,181,391 B1 | 5/2012 | Giacomantonio | |
| 8,505,238 B2 | 8/2013 | Luebbers | |
| 9,814,186 B2 | 11/2017 | Anderson | |
| 9,937,218 B2* | 4/2018 | Towle | A61K 36/185 |
| 10,517,911 B2* | 12/2019 | Gharib | A61K 9/4875 |
| 2008/0172938 A1 | 7/2008 | Azoulay | |
| 2012/0291349 A1 | 11/2012 | Teng | |
| 2014/0110329 A1 | 4/2014 | Kemper et al. | |
| 2014/0130413 A1 | 5/2014 | Storey | |
| 2014/0130414 A1 | 5/2014 | Storey | |
| 2014/0137472 A1 | 5/2014 | Anderson | |
| 2014/0144079 A1 | 5/2014 | Lin | |
| 2016/0029581 A1 | 2/2016 | Martin | |
| 2016/0066525 A1 | 3/2016 | Duquesnay | |
| 2017/0202162 A1 | 7/2017 | Dufresne | |
| 2017/0202164 A1 | 7/2017 | Dufresne | |
| 2018/0000029 A1 | 1/2018 | Martin | |
| 2018/0214790 A1* | 8/2018 | Tucker | B01D 3/40 |
| 2018/0228104 A1 | 8/2018 | Mirzeabasov | |
| 2018/0369714 A1* | 12/2018 | Coffin | F04B 41/02 |
| 2018/0369716 A1* | 12/2018 | Robbins | B01D 11/0223 |
| 2019/0153484 A1* | 5/2019 | Bray | A61K 36/185 |
| 2019/0183848 A1* | 6/2019 | Sorbo | A61K 31/352 |
| 2019/0209633 A1* | 7/2019 | Speier | A61K 9/006 |

FOREIGN PATENT DOCUMENTS

| | | |
|---|---|---|
| CH | 690835 | 2/2001 |
| EP | 0288670 | 11/1988 |
| WO | 9500007 | 1/1995 |
| WO | 0232593 | 4/2002 |

OTHER PUBLICATIONS

DaPorto, C. et al. Separation of Aroma Compounds From Industrial Hemp Inflorescences by Supercritical CO2 Extraction and On-Line Fractionation. Industrial Crop and Products 58:99-103, 2014. (Year: 2014).*

* cited by examiner

*Primary Examiner* — Ralph J Gitomer
(74) *Attorney, Agent, or Firm* — Holzer Patel Drennan

(57) ABSTRACT

A system selectively extracts compounds form plant material. A liquid solvent is introduced to the material and through subsequent cycles of gradually increasing the temperature and pressure of the extraction chamber, various compounds can be selectively harvested from the plant material. The desirable compounds can each be routed to an individual collection chamber for individual extraction and storage. This allows volatile compounds and non-volatile compounds to be selectively extracted and stored separately.

22 Claims, 7 Drawing Sheets

Sample Recipe - Co2 Extraction

| | Step | # | Step # |
|---|---|---|---|
| BATH 1 | Purge | | 0 |
| | Fill | | 1 |
| | Boost | 400 psi | 2 |
| | Additional Fill | | 3 |
| | Recirculate | 5 min | 4 |
| | Drain / Recover | | 5 |
| BATH 2 | CoSolvent Add | 200 ml | 6 |
| | Fill | | 7 |
| | Additional Fill | | 8 |
| | Boost | 950 psi | 9 |
| | Recirculate | 20 min | 10 |
| | Drain / Recover | | 11 |
| BATH 3 | CoSolvent Add | 200 ml | 12 |
| | Fill | | 13 |
| | Additional Fill | | 14 |
| | Boost | 950 psi | 15 |
| | Recirculate | 20 min | 16 |
| | Drain / Recover | | 17 |
| BATH 4 | CoSolvent Add | 0 | 18 |
| | Fill | | 19 |
| | Additional Fill | | 20 |
| | Boost | 950 psi | 21 |
| | Recirculate | 20 min | 22 |
| | Drain / Recover | | 23 |
| BATH 5 | CoSolvent Add | 0 | 24 |
| | Fill | | 25 |
| | Additional Fill | | 26 |
| | Boost | 1800 psi | 27 |
| | Recirculate | 30 min | 28 |
| | Drain / Recover | | 29 |
| | Vent | | 30 |

Fig. 4

SELECTIVE EXTRACTION OF BOTANICALS FROM PLANT MATERIAL

CROSS REFERENCE TO RELATED APPLICATION

This application is based on and claims priority to U.S. Provisional Application No. 62/588,108, filed on Nov. 17, 2017, entitled, "SELECTIVE EXTRACTION OF BOTANICALS FROM PLANT MATERIAL," the contents of which are herein incorporated by reference.

BACKGROUND

Typical system and methods for extracting botanicals from plant materials rely upon supercritical fluid extraction, in which the liquid solvent is taken to a temperature and pressure above its critical point. This allows extraction and separation of complex substances into basic components.

However, using a solvent in its supercritical state is an aggressive procedure and destroys many of the desirable volatile compounds within the plant material. Moreover, in a supercritical fluid extraction process, at least some of the botanicals will aerosolize and spread throughout the extraction equipment, necessitating time-consuming and costly cleanup to avoid contamination with subsequent extraction processes.

Furthermore, supercritical fluid extraction results in an impure product that requires a winterization purification step, which consists of soaking the extract in alcohol and freezing it in order to separate the residual products. However, the added alcohol is chemically similar to terpenes which are desirable botanicals that may be found in the plant material, and the alcohol bonds to the terpenes thereby introducing impurities. Moreover, the alcohol is a flammable solvent and creates hazardous conditions.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

FIG. 4 is an example recipe for extracting botanicals using $CO_2$.

DETAILED DESCRIPTION

Figure 1:
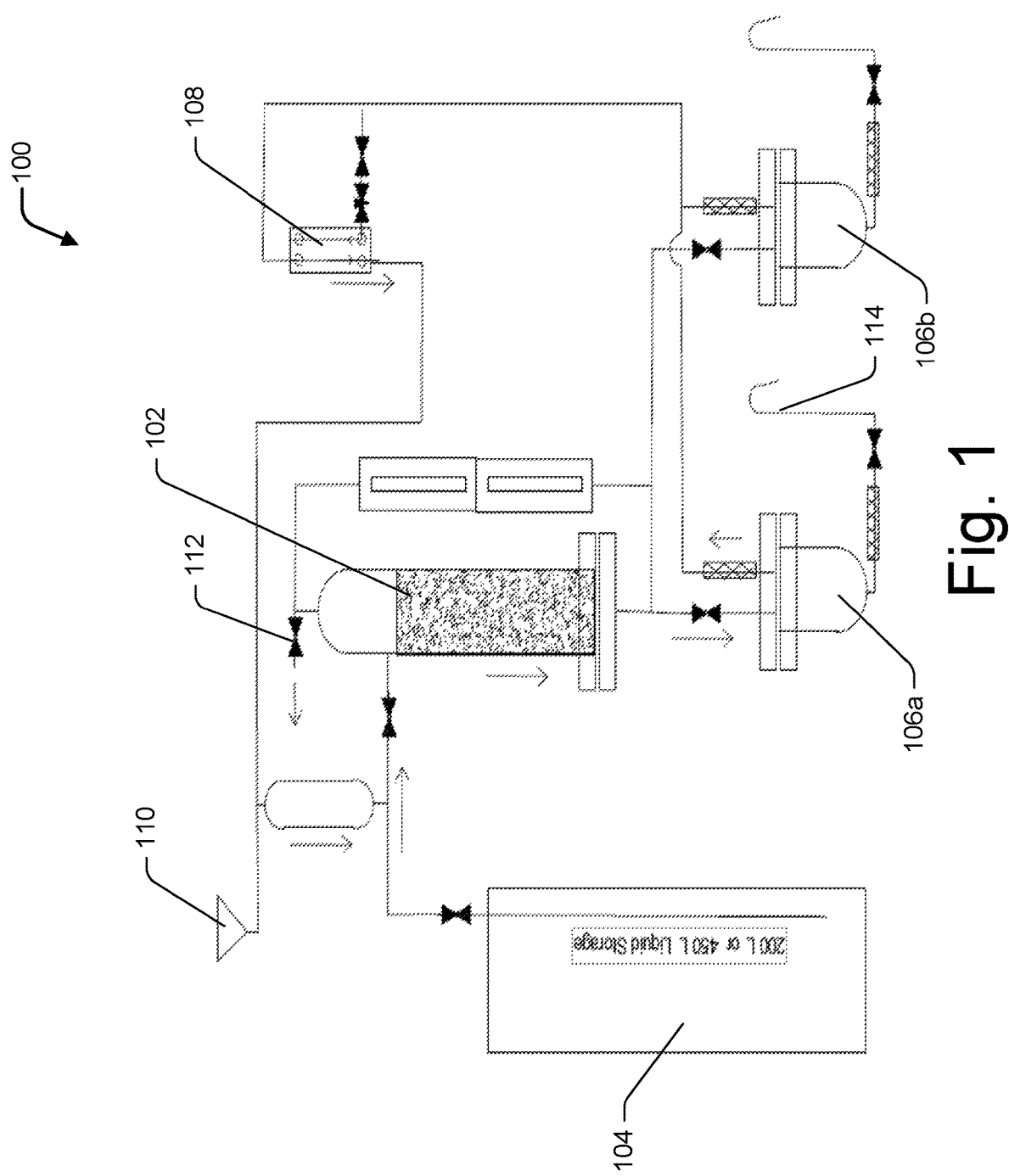
FIG. 1 is a block diagram illustrating a process flow of an embodiment of a system for selective extraction of botanicals.

This disclosure describes, in part, systems and techniques for selective extraction of botanicals from plant materials. That is, the system fractionates the plant material and various compounds can be selectively extracted.

According to some embodiments, a system for selectively extracting compounds from plant material includes an extraction vessel, a liquid storage tank, one or more collection chambers, and a heat exchanger. The system can be operated to extract the compounds in the absence of alcohol. This provides several benefits, primarily the ability to selectively extract terpenes, which are oftentimes destroyed or removed when separating the alcohol.

In some cases, the system operates thermodynamically in the absence of electricity. That is, thermodynamic principles and gravity drive the extraction process, including pressurization, fluid flow, and solvent recovery, among others.

An agitator may be used to reposition the plant material during an extraction process. The agitator may rotate, stir, shake, tumble, spin, or otherwise reposition the plant material to inhibit channeling of the solvent through the plant material.

In some instances, liquid carbon dioxide is used as the solvent in order to extract the botanicals. The liquid carbon dioxide may be used in a sub-critical state, and is preferred when extracting terpenes since these are typically destroyed during typical $CO_2$ supercritical fluid extraction techniques.

A heat source may be used to raise the temperature of one or more materials within the extraction vessel, such as the $CO_2$, and can be used to regulate the pressure within the extraction vessel. In fact, in those embodiments in which the system is closed, the pressure is maintained steady throughout the extraction, separation and collection chambers without wide pressure differentials, which may also destroy the desirable terpenes. The heat source may be heated liquid, such as water, oil or a glycol water mixture, or may alternatively be provided by an external heater.

There may be multiple collection chambers each used independently during different stages of the extraction for collecting and storing compounds separately with little to no cross-contamination. Separated compounds include volatile, non-volatile and lipids.

According to one embodiment, a method of extracting cannabinoids from plant material includes subjecting the plant material to liquid carbon dioxide at a pressure of below 500 psi and a temperature below 0° C. In some cases, this pressure and temperature will extract terpenes found within the plant material. The liquid carbon dioxide can be heated to a temperature high enough to convert from liquid to gas, but low enough that the terpenes will not become vapor, thus leaving an extracted terpene, which can be collected in a collection chamber. Once the carbon dioxide has boiled off, it can be sent through a heat exchanger and condensed back into a liquid form.

After the terpenes are collected, the plant material may be subject to liquid carbon dioxide at a pressure of between about 500 psi and 950 psi at a temperature of between about 0° C. and 28° C. In some cases, this pressure and temperature will extract non-volatile cannabinoids from the plant material, such as, for example, Δ9-tetrahydrocannabinol and cannabidiol, among others.

The extracted terpene can be stored in a first collection chamber, and the extracted non-volatile compound can be stored in a second collection chamber. This allows the compounds to be extracted and stored separately, avoiding the processing steps lipids or non-volatiles require which impact the quality or yield of the volatiles. They can be mixed after any post processing has been performed in desired ratios to produce various products.

In some cases, a modifier can be added to the carbon dioxide to increase the carbon dioxide extraction efficacy. For instance, in some cases, adding a small amount of co-solvent, such as an alcohol, can increase the solvency power of the $CO_2$. However, in some cases, the extraction is performed in the absence of alcohol. An alcohol may be added when extracting the non-volatiles, and may be avoided when extracting the volatiles since alcohol and terpenes are chemically similar and have a tendency to combine, thus destroying the terpenes, as such. While botanical compounds are in the solution of $CO_2$ and modifier they can be filtered to further remove unwanted lipids, fats, and waxes.

In some instances, the extraction is performed at a steady pressure. That is, once the pressure is established by adding heat to the system or manipulating the pressure to change temperature, the pressure remains relatively constant throughout the extraction process. In some typical extraction processes, pressure gradients are used to encourage the extraction; however, such pressure gradients may destroy the desirable volatile compounds, so in some cases, the extraction is performed at a relatively steady pressure throughout the chambers in the process loop.

According to an embodiment, a method of extracting botanicals includes extracting, from a *Cannabis* plant in a first bath, one or more terpenes. The terpenes can be collected in a first collection chamber. Cannabinoids may subsequently be extracted from the *Cannabis* plant by a second bath and stored in another collection chamber separated from the terpenes. The terpenes and cannabinoids may be mixed in any desired ratio to produce a finished product.

The terpenes may be extracted by subjecting the plant to sub-critical liquid carbon dioxide at a pressure of less than about 500 psi and a temperature of less than 0° C. This is a relatively mild process that preserves the terpenes. The pressure may be controlled by the addition of heat to boil at least some of the liquid carbon dioxide. The heat may be provided by water.

Collecting the cannabinoids may be performed in sub-critical liquid carbon dioxide at a pressure of between about 500 psi to about 950 psi and at a temperature of between about 0° C. and 28° C. This is a slightly more aggressive bath than that used to extract the terpenes. By varying the temperature and pressure of the carbon dioxide, various compounds can be selectively and sequentially extracted and stored separately to avoid cross-contamination.

The cannabinoids may be extracted through repeatedly flowing and purifying the liquid carbon dioxide through the plant at the process conditions. The extraction process may be repeated 3, 4, 7, 8, or more times.

The plant material may be subject to multiple baths at different parameters to seek differing compounds. This includes compounds soluble in liquid $CO_2$. For compounds not soluble in liquid $CO_2$ a separate bath may use supercritical carbon dioxide, and these other compounds can be stored in a third collection chamber separate from the terpenes and cannabinoids.

These and other features will become apparent by reference to the figures and the following description.

FIG. 1 illustrates a block diagram showing several components of one example system 100 and a general process flow for selective extraction of compounds. The illustrated system includes an extraction vessel 102, a solvent storage tank 104, one or more collection chambers 106a, 106b, a heat exchanger 108, and in some embodiments, an additive port 110. These components may be in fluid communication with one another through the use of tubing, valves, and other devices to allow the process to proceed as described herein.

The arrows shown throughout the drawing generally describe the direction of fluid and gas flow. The illustrated process begins after the botanical material has been loaded into the extraction vessel 102. One or more processes can be performed on the plant material to extract desired botanicals while avoiding un-wanted compounds, which may include, without limitation, volatiles, non-volatiles, fats, lipids, waxes, water, and pigments.

In use, plant material is introduced to the extraction vessel 102. The amount and type of plant material may vary depending on the desired finished product. In some examples, the extraction vessel is capable of holding a high pressure, such as about 3000 psi and may be made of stainless steel or another suitable material.

The gas within the extraction vessel 102, primarily air, is purged by introducing the desired solvent in a gaseous form. According to some examples, carbon dioxide ("$CO_2$") is used as the solvent and gaseous $CO_2$ may be used to purge the extraction vessel 102. The air may be purged, such as by venting gaseous $CO_2$ into the extraction vessel 102 and opening a bleed valve, 112 and venting the air and some of the gaseous $CO_2$. Using $CO_2$ as an example solvent, liquid $CO_2$ may be stored in the storage tank 104, and introduced into the extraction vessel 102 in its liquid form. $CO_2$ is relatively cheap, widely available, chemically inert, non-toxic, non-flammable and readily available at high purity. Moreover, $CO_2$ exhibits supercritical behavior at relatively mild conditions and can safely be vented to the atmosphere, and does not leave organic residues, thus making it a suitable solvent according to some embodiments described herein. For explanatory purposes of some of the embodiments disclosed here, $CO_2$ will be used as the solvent, without limiting its usage in all cases.

The material within the extraction vessel 102 responds in different ways to various temperatures and pressures. As a consequence, the material can be exposed to sequentially increasing temperatures and pressures to extract various botanicals from the material.

Heat may be added to the extraction vessel 102, such as by a heater, heat transfer of a liquid medium, frictional agitation, or through some other heat transfer process. As heat is applied, the pressure within the extraction vessel 102 rises. Once the heat within the extraction vessel 102 is within a first desired range, heat is no longer applied and the temperature and pressure within the extraction vessel 102 stay within a desired range.

The liquid solvent, $CO_2$ in some cases, is forced through the material and it then continues to a collection chamber 106a along with botanicals picked up from the plant material. In the collection chamber 106a, heat is applied and the liquid solvent is boiled off into a gas which proceeds to a heat exchanger 108. The gas is condensed back into a liquid at the heat exchanger 108 and returned via gravity to the storage tank 104 or extraction vessel 102. The botanical left in the collection chamber 106a is under pressure within the closed system and may be withdrawn, such as through a spigot 114, or some other selective withdrawal mechanism.

One or more collection chambers 106a, 106b, . . . , 106n may be provided in order to separately collect the various fractionated botanicals that may be extracted from the plant material without causing cross contamination between the botanicals in the separate collection chambers 106a, 106b.

The illustrated system is a closed system and the solvent changes phase from a liquid, to a gas, and is condensed back into a liquid and returned to take part in additional processing cycles. Any remaining gas in the system may be vented and purged from the system. As described, the process may be repeated at different temperatures and pressures to extract various botanicals in sequence, which will be described in additional detail below.

During some cycles, it may be desirable to add one or more modifiers to the system, such as by introducing a modifier by way of an additive port 110. The modifier may be added to the liquid solvent as it is introduced into the extraction vessel 102. In some cases, the modifier is selected to result in a more robust extraction in a shorter period of time than without the modifier. In some cases, the modifier may be an alcohol.

As shown in FIG. 1, a closed system is provided that operates at a steady pressure and temperature, until the solvent is condensed. The relatively steady pressure preserves the volatile compounds that are typically destroyed with the extraction processes that operate in the solvent supercritical phase. Moreover, the illustrated system uses direct refrigeration, which may be provided by the solvent itself, without the need for external chillers or pumps. The illustrated system is thermodynamically driven, meaning that through the application of heat, the pressure within the system is brought to a desired pressure, which causes the solvent and botanical to flow through the system.

Figure 2:
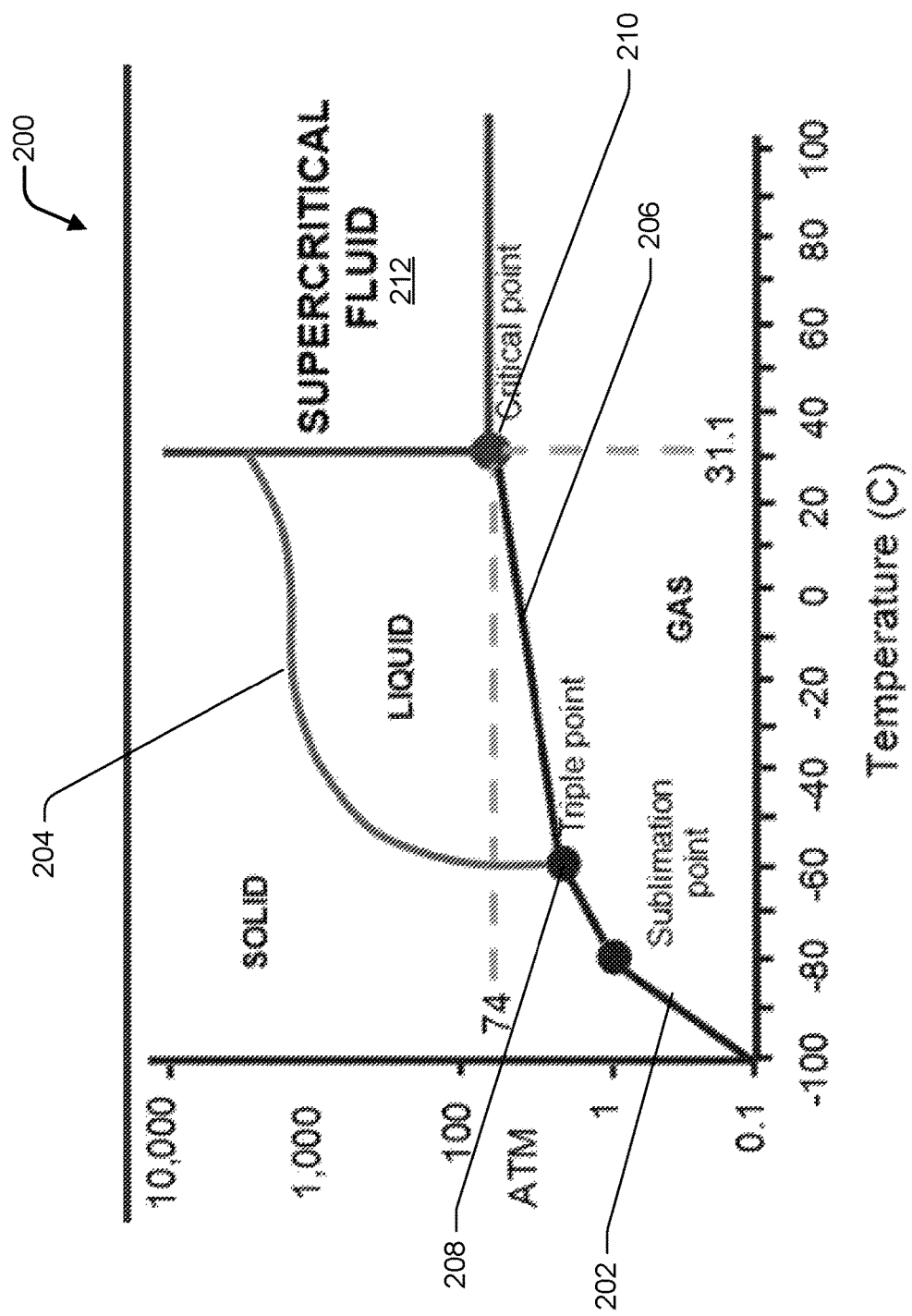
FIG. 2 is a phase diagram of carbon dioxide ($CO_2$).

FIG. 2 illustrates a phase diagram of $CO_2$ 200. As illustrated, $CO_2$ has 3 stable phases: solid, liquid, and gas. The diagram is divided into three regions by boundary lines that separate each phase from one another. The boundary lines represent the equilibrium between any 2 of the phases. For example, the boundary line 202 between the solid and gas phase is a sublimation line, meaning that for a constant pressure, increasing the temperature across the boundary line 202 causes a phase change from solid to gas. For example, at 1 atm of pressure, $CO_2$ is in a solid form below $-78.5°$ C., and in a gaseous phase above this temperature.

Another boundary line 204, between the solid and liquid phase, represents a melting line. That is, for a constant pressure, increasing the temperature above the boundary line 204 causes a phase change from solid to liquid.

Finally, the boundary line 206 between the liquid and gas phase represents a saturation line. Thus, for a constant pressure, increasing the temperature above the saturation line 206 causes a phase change from liquid to gas.

A triple point 208 exists at which all three phases can coexist, and a critical point 210 describes a temperature and pressure above which the fluid can be described as supercritical. When a fluid is subjected to a temperature and pressure above its critical point, the fluid exhibits an intermediate behavior between a liquid and a gas. For example, a fluid in the supercritical region 212 has a density similar to a liquid, a viscosity similar to a gas, and a diffusivity intermediate that of a liquid and a gas.

Many current extraction techniques, especially those using $CO_2$ as a solvent, are designed to perform the extraction with the $CO_2$ in the supercritical region. This has several disadvantages. It requires a more complex arrangement of pressure chambers to vary the pressure, along with external pumps, heaters, and/or chillers to cause the change in pressure and to condense the $CO_2$ back into a liquid. Moreover, using supercritical $CO_2$ is an aggressive process and will typically destroy terpenes that may be a desirable extracted botanical by entraining them in the gas phase exposing them to heat and compression or by combining them with other compounds. Finally, the process is relatively slow, which directly affects the production rate of the finished product.

One particular advantage to some of the embodiments disclosed herein is the thermodynamically balanced system to run at a relatively low pressure below the supercritical region. Furthermore, operating below the supercritical region avoids the necessity of additional processing steps that may include introduction of flammable solvents and further destroys desirable botanicals.

Figure 3:
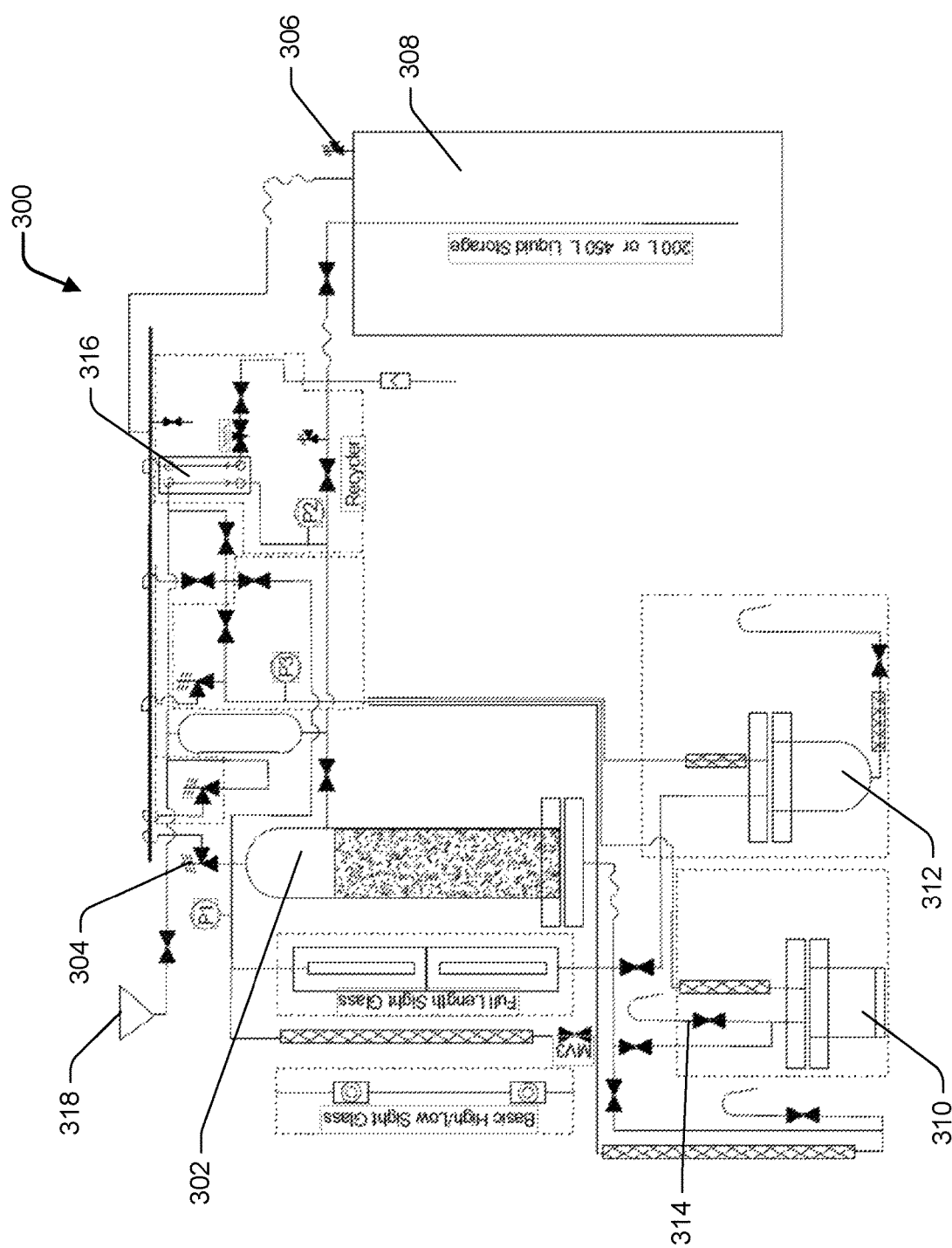
FIG. 3 is a block diagram illustrating an exemplary system for selective extraction of botanicals.

FIG. 3 illustrates another example extraction system 300 that can be used according to the methods described herein. An extraction vessel 302 is configured to hold the material, and may be a pressure vessel. In some cases, the pressure throughout the system may reach 300 psi, 500 psi, 700 psi, 800 psi, or 900 psi or higher. One or more pressure relief valves 304 may be provided throughout the system in order to provide a safety release in the event that pressure within the system reaches a pressure sufficient to open the pressure relief valve 304. The pressure relief valves can be configured to open at any desired pressure and may be opened at differing pressures depending on where in the system the pressure relief valve is located. For example, a pressure relief valve 306 in communication with the liquid storage tank 308 may have much lower opening threshold pressure than a valve 304 located in communication with the extraction vessel 302.

In some instances, the extraction vessel 302 is configured with a mechanism to rotate the sample therein. For instance, one phenomenon that reduces the efficiency of an extraction process is known as channeling, where the solvent takes the path of least resistance through the material, which inhibits the solvent from being distributed throughout the material. By moving the material while being subject to the solvent, the solvent is able to more evenly flow through the material. In some cases, the material may be place within a rotating basket. Of course any suitable method of repositioning the material may be utilized with similar beneficial effects, such as, for example, stirring, shaking, tumbling, vibrating, spinning, mixing, or some other way of repositioning the material to inhibit channeling.

As the solvent flows through the material, the solvent picks up botanical compounds from the material, where it flows to one or more collection chambers 310, 312. The solvent and botanical may enter the collection chamber 310 through the force of gravity, or through the application of pressure within the system. In some cases, the pressure within the collection chamber 310 is nearly the same as the pressure with the extraction vessel 302, and the solvent flows into the collection chamber 310 by the force of gravity. In some cases, the solvent is not miscible with the botanical and therefore can be separated from the botanical through the application of heat, which can be used to boil off the solvent, thereby leaving the botanical in the collection chamber 310. The botanical can be withdrawn from the collection chamber 310, such as by opening a spigot 314, or a valve. In some cases, the collection chamber 310 may have a door, window, lid, or some other selectively openable aperture to allow withdrawal of the botanical collected therein.

A second collection chamber 312 may be provided to collect additional botanicals which may be kept separated from a firstly collected botanical that has been collected within the first collection chamber 310.

As the solvent within the collection or separation chamber is boiled off, it passes to a heat exchanger 316 where it can be cooled, condensed, and returned to the liquid storage tank 308. The liquid storage tank 308 stores liquid solvent in a sufficient volume to carry out the extraction processes. In some cases, the solvent is recirculated and used for multiple extraction cycles. The liquid solvent may provide refrigeration for the thermodynamic system and may be at least partially responsible for adjusting the pressure within the system based upon the temperature.

An additive port 318 may be in fluid communication such that additives may be mixed with a portion of the solvent in the extraction vessel 302. In some cases, the additive port 318 allows an additive, (e.g., a modifier) to be added to the solvent just prior to it entering the extraction vessel 302. The additive may speed up the extraction process, influence the efficiency at which the solvent is able to liberate the botanical, or mix with the botanical to provide a modified botanical.

The system may run sequential extraction cycles at various pressure and/or temperatures and with or without various additives. For instance, a first extraction cycle may be run at a relatively low temperature and pressure to extract volatiles from the material. The volatiles may be captured in a first collection chamber 310. The volatiles in *Cannabis* belong to the terpenes family. The terpenic profile varies greatly across different *Cannabis* varieties. The primary terpenes are myrcene, β-caryophyllene, α-pinene, β-pinene, limonene, linalool and α-humulene.

A second extraction cycle may be run at a higher temperature and pressure and non-volatiles may be removed from the material and captures in a second collection chamber 312. The non-volatiles may be found in the leaves and inflorescences of the plant and are part of the cannabinoids family. The two most well-known non-volatile compounds are Δ9-tetrahydrocannabinol ("Δ9-THC"), and cannabidiol ("CBD"). Other non-volatile compounds are present, such as cannabichromene, cannabigerol, and cannabinol. The multiple collection chambers 310, 312 allows the system to selectively extract different botanicals and store them separately while inhibiting contamination of one botanical with another.

The different botanicals may have different viscosities, and the system can be run within a desired temperature range to influence the flowability of the botanical in order to efficient collect it into the collection chamber 310. For instance, terpenes typically have a low viscosity and readily flow. However, cannabidiol and other cannabinoids may have a higher viscosity and is more resistant to deformation by shear or tensile stresses. However, the application of heat can be used to encourage the higher viscosity materials to flow for a more complete collection.

In some cases, the desired product can be selectively tailored for its intended use. For example, where it is desirable for the end product to readily flow, a higher percentage of terpenes may be collected within the collection chamber along with cannabinoids. Similarly, where a thicker product is desired, a lesser amount of terpenes or other volatiles may be collected.

FIG. 4 illustrates a sample recipe for extracting desired products. At step 0, the plant material is inserted into the extraction vessel and the system is purged of atmospheric gases. At step 1, the extraction vessel is filled with solvent, which in the illustrated recipe, is $CO_2$. The pressure within the extraction vessel is raised, such as to 400 psi and the first extraction begins. In some instances, volatiles are the first to be extracted because they are extractable at the lowest temperature and pressure. These are the compounds that are largely responsible for producing aroma and taste of a botanical. The relatively low pressure and temperature allows the system to capture these compounds in a high concentration with relatively little contamination from other compounds. Other compounds may be extracted in a later process that occurs at a higher temperature and pressure.

The first extraction cycle, also referred to as Bath 1, may be repeated or elongated depending on the available harvestable volatiles in the starting material. The Bath 1 parameters may be different depending on the botanical, but may typically fall within the range of from about 300 psi to about 500 psi, or any value therebetween. As shown at step 2, a pressure of about 400 psi is used with the illustrated recipe. The temperature is typically within the range of from about −20° C. to about 0° C. The extraction vessel may be filled to about 50% to 80% with $CO_2$ solvent, and additional solvent may be added, at step 3. At step 4, the solvent is recirculated throughout the material for a duration of anywhere between about 1 minute and 20 minutes, and is about 5 minutes in the illustrated recipe. Bath 1 typically does not require any modifiers, but one or more may be added as desired depending on the starting material and the desired finished product. The extracted botanicals from Bath 1 may be stored in a collection chamber and the solvent can be drained, boiled off from the extracted botanicals, and returned to the liquid storage tank for another cycle or to the extraction vessel for another pass.

As illustrated, Bath 2 may be performed with the material remaining in the extraction vessel by adding solvent to the extraction vessel where it may be filled to 50% to 80% of the capacity of the extraction vessel. At step 9, the pressure is raised to a pressurization that is typically higher than in Bath 1, and as illustrated, is raised to about 950 psi. At this pressure, non-volatiles may be extracted from the material. The precise pressure range may be selected to extract the desired non-volatile compounds while ignoring the undesired compounds, and leaving them in the material.

In some cases, the early baths that extract non-volatile compounds may be collected in the same collection as the volatile compounds. This may apply to parameters that are selected to avoid extracting unwanted compounds that need post processing to rectify. The volatile and non-volatile compounds may be extracted together in those cases where the desired finished product is a full spectrum representation of the botanical.

The bath parameters may further be selected to tune the ratio of individual desired compounds, and thus increase the ratio of one botanical over another in the finished product.

As illustrated, Bath 3 and Bath 4 may repeat the parameters of Bath 2, in order to extract a relatively high percentage of the available non-volatile compounds. Of course, the process may be repeated more, or fewer, times depending on the efficacy of the starting material and the desired finished product.

During one or more Baths, an optional modifier may be added to the $CO_2$ and can be used to tune the $CO_2$, the modifier itself, or both. For example, when the characteristics of the $CO_2$ don't correspond with the desired compounds being extracted, the modifier can enhance the extraction process. Some examples of this are a need to overcome issues of polarity, moisture, solvency power, among others. The modifier may be added to the system and then pressurized, or pressurized as adding the modifier. It may also be added to the system and exposed to the botanical material in concentration, or diluted with $CO_2$. In many cases, modifiers are selected to be soluble in $CO_2$ and/or contain additives to create a bond with $CO_2$. $CO_2$ without the modifier can be used to rinse the remaining modifier from the botanicals so there is little residual modifier left in the spent material. Some examples of common modifiers include, but are not limited to, ethanol, methanol, water, acetic acid, terpenes, glycol, acetone, ketones, hexane, butane, and propane, among others.

Extraction of nonvolatile compounds typically occurs at a pressure between about 500 psi and 950 psi at a temperature of about 0° C. to about 28° C. The liquid level in the extraction vessel may be on the order of about 50% to about 80%, or more. The solvent contact time with the material may be on the order of about 1 minute to about 20 minutes. In some cases where a modifier is desirable, it can be added in a concentration of about 1% to 10% of the $CO_2$ volume. In some instances, the modifier is undiluted and exposed to the material at a 100% concentration, and can subsequently be rinsed with $CO_2$. These nonvolatile extraction parameters are reflected in Baths 2, 3, and 4 in the illustrated recipe and may be repeated more times, or fewer times. Additionally, the baths can have different parameters that may target different nonvolatile compounds.

Any remaining desirable and obtainable compounds can be extracted through a more aggressive extraction approach. In some instances, heat may be added to the system to increase the temperature above about 31.1° C. and above about 1090 psi for supercritical fluid extraction ("SCFE"). In many cases, SCFE is not selective between desired compounds and contaminants such as fats, lipids, waxes, water, and plant pigments. While there will be a small amount of desired compounds removed with these aggressive baths, it may require additional time to separate the desirable components from the contaminants. However, there are some cases that may desire these unwanted compounds, so the process may be run by starting with relatively low temperature and pressure and sequentially increasing both to selectively fractionate and extract desired botanicals in sequence.

The parameters for extracting the remaining compounds varies with each botanical, but may be within the range of from about 1050 psi to about 1800 psi at a temperature between about 31° C. and 40° C. The material may be washed with solvent for a period of about 1 minute to about 60 minutes, or more. If desired, a modifier may be added to the solvent in a concentration of about 1% to 10% of the solvent volume. In some cases, the modifier may be used undiluted and subsequently washed from the material by solvent. An example process is illustrated as Bath 5, and this may be repeated one or more times.

At the end of the extraction process, the $CO_2$ is either recovered, such as by draining the liquid $CO_2$ to the storage tank and condensing the gaseous $CO_2$ to a liquid and returned to the storage tank. Any remaining gaseous $CO_2$ in the system may be vented to the atmosphere.

As described by the process illustrated in FIG. 4, the end result is three fractions: volatiles, non-volatiles, and non-volatiles mixed with contaminants. These fractions may be collected through subsequent Baths and stored separately in individual collection chambers. In some cases, the collection of non-volatiles may have the modifier removed (if any) and may be mixed with the volatiles in an amount needed to reach the desired finish product.

Figure 5:
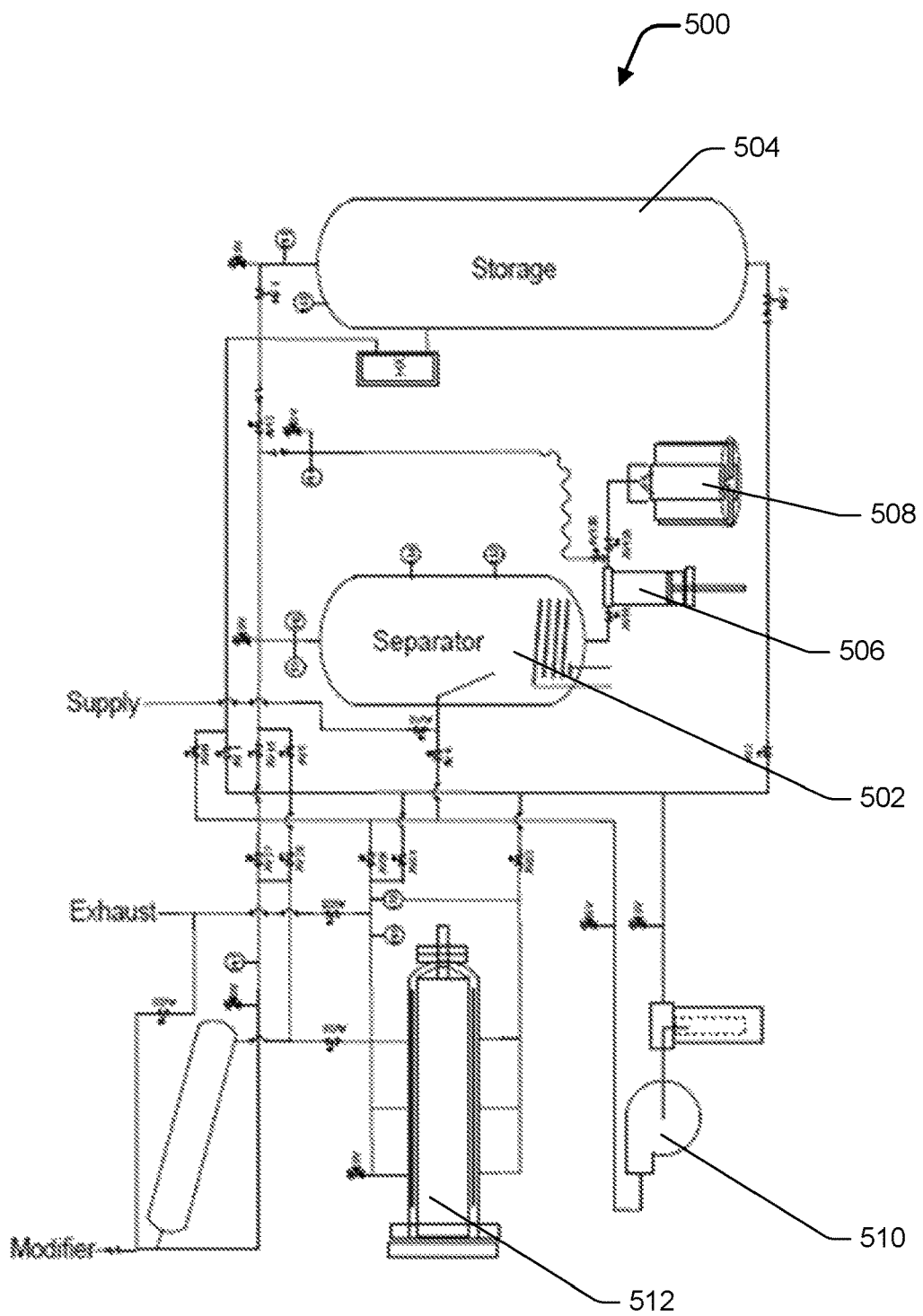
FIG. 5 is another block diagram illustrating an exemplary system for selective extraction of botanicals.

FIG. 5 illustrates another example of a system 500 designed for extraction and has the addition of one or more pumps to help pressurize the system and encourage fluid flow. A separator 502 chamber houses the material and is in fluid communication with a liquid solvent tank 504. As the solvent passes through the material, it drains to one or more collection chambers 506, 508. The liquid solvent may be boiled off, condensed, and returned to the storage tank 504. A pump 510 may optionally be used to encourage fluid circulation through the system. In addition, one or more chillers 512 may be employed to vary the temperature of the solvent.

The illustrated system 500 provides a semblance of automation. That is, the addition of the pump 510 and/or chiller 512 can be controlled through any computerized controller to run through the extraction cycles, as desired. In some instances, a recipe can be input into a computerized controller, which can then carry out the recipe through various Baths at the desired parameters. For instance, material can be loaded into the extraction vessel 512 manually (or automatically), and a computerized controller can open the necessary values and pressurize the system to provide solvent into the separator. The material may be repositioned or otherwise agitated through mechanical means for a sufficient duration, and the controller can open additional valves to drain the solvent and botanicals to the collection chamber 506.

The controller can cause the temperature in the separator 502 to increase to boil off the solvent, initialize the heat exchanger to condense the gaseous solvent and return it in a liquid form to the storage tank 504. The controller can execute instructions to process the material through one or more sequential baths and provide communication for the botanicals to be deposited and stored in an appropriate collection chamber 506, 508.

Figure 6:
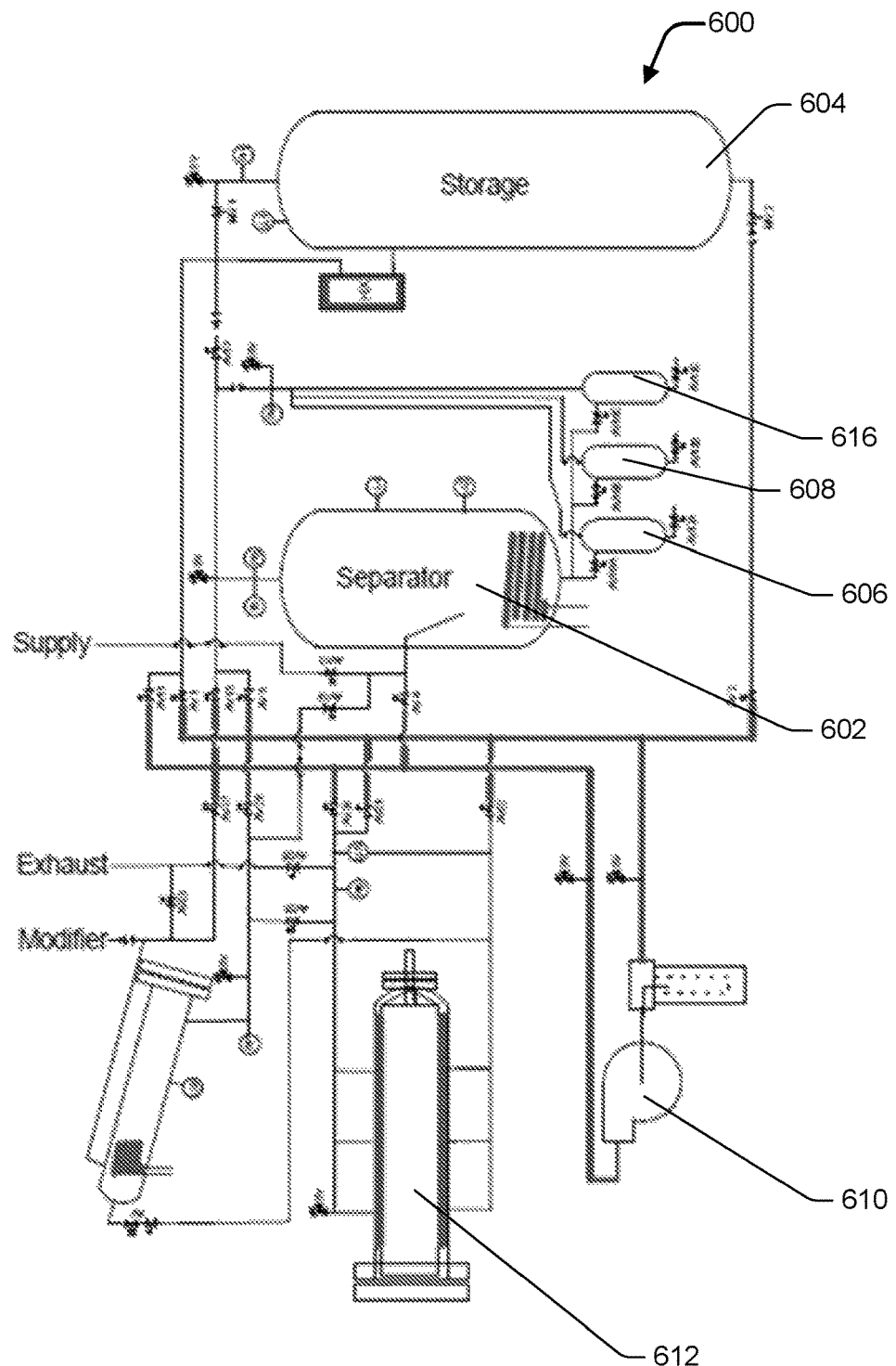
FIG. 6 is another block diagram illustrating an exemplary system for selective extraction of botanicals.

FIG. 6 illustrates a schematic diagram of another embodiment of an extraction system 600. A separator 602 chamber houses the material and is in fluid communication with a liquid solvent tank 604. As the solvent passes through the material, it drains to one or more collection chambers 606, 608. The liquid solvent may be boiled off, condensed, and returned to the storage tank 604. A pump 610 may optionally be used to encourage fluid circulation through the system. In addition, one or more chillers 612 may be employed to vary the temperature of the solvent.

As illustrated, multiple collection chambers may be utilized with the system to selectively capture and store compounds extracted from the material. As an example, a first bath operating at a relatively low temperature and pressure can extract volatiles, such as terpenes, from the material which can be stored in a first collection chamber 606. After the terpenes are harvested and collected, the first collection chamber 606 can be segregated from the system, such as by shutting a valve 614. A subsequent bath can extract non-volatiles, such as cannabinoids, which can be stored in a second collection chamber 608. A subsequent bath can extract remaining obtainable compounds, which can be stored in a third collection chamber 616. By selectively extracting and storing the various obtainable compounds, the can be mixed in any desired ratio to produce a desired finish product.

According to some embodiments, the system 600 can accept 100 g of material, and depending on the potency of the material, the extraction process can deliver 100 g of finish material in roughly two hours. According to other embodiments, 125 lb of material can be added to the extraction vessel and about 12.5 lb of finish material can be harvested. On average, a 10% yield is feasible depending on the potency of the starting material. In some cases, the effective yield may be as high as 20% or higher. Different finish products require different ratios and types of terpenes and cannabinoids, so the ability to be able to selectively collect and store these compounds makes mixing particular products efficient.

As described, the system and processes are able to effectively extract botanicals by maintaining a solvent, such as $CO_2$, in its sub-critical phases. Moreover, there is no need to purify the result through a winterization process, which would destroy the desirable terpenes, and add a harmful flammable solvent. The disclosed system and process provides an efficient and safe method for selectively extracting the desired compounds from plant materials.

The result is that the system is able to modify its operating conditions to tune terpene and cannabinoid ratios. $CO_2$, in its gentle liquid state, is able to target essential components while ignoring contaminants that would otherwise require post processing. The liquid $CO_2$ phase is amenable to co-solvent modifiers or additives that expand the ranges for total extractions.

Figure 7:
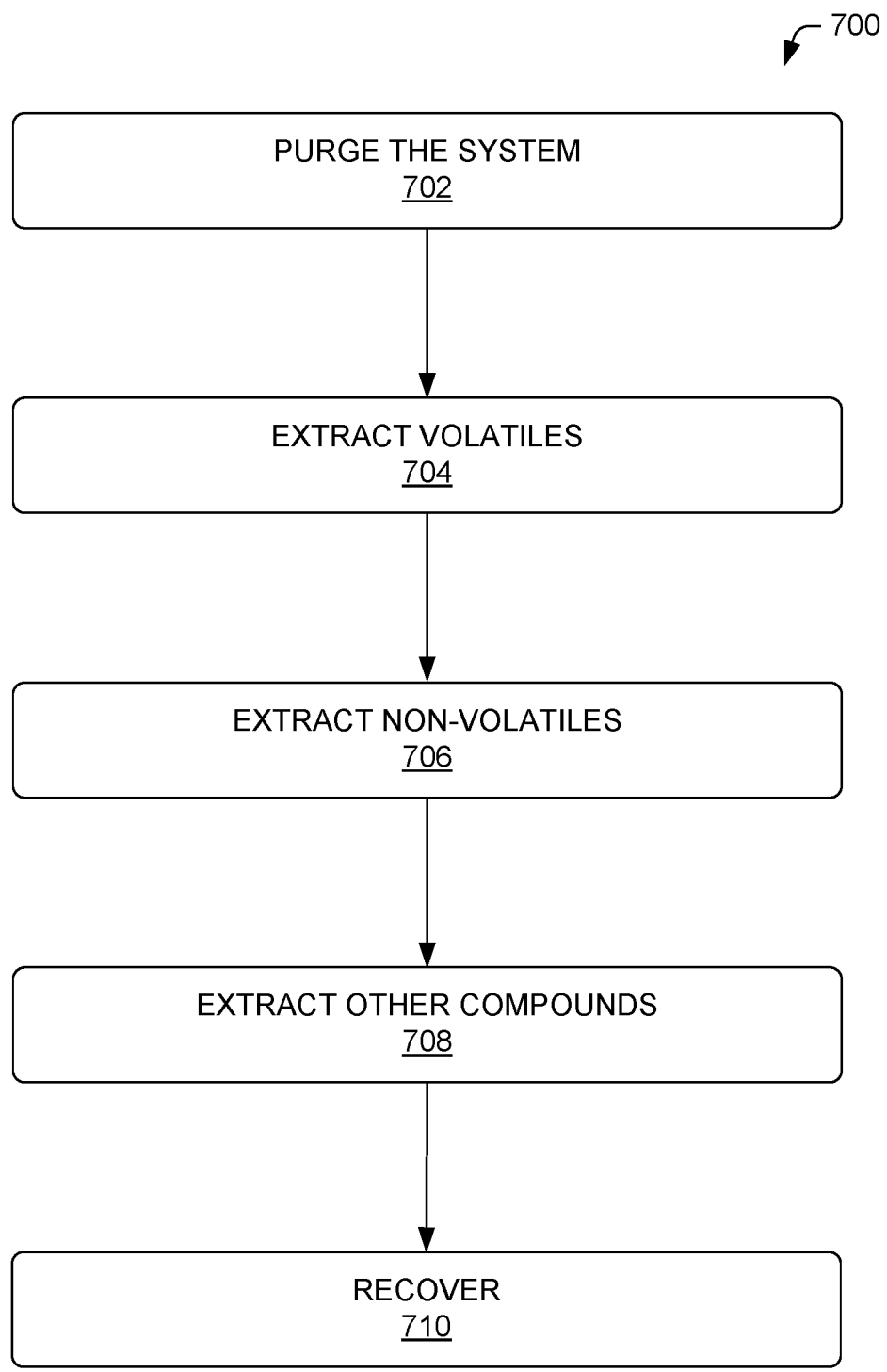
FIG. 7 is a process flow for extraction of botanicals from plant material.

FIG. 7 is a flow diagram illustrating a basic process flow. At block 702, material is loaded into the system and the system is purged of air, such as by forcing gaseous $CO_2$ into the system, allowing it to settle to the lower portions and then venting the air from a high portion. At block 704, volatiles are extracted. This may be accomplished by introducing liquid $CO_2$ into the extraction vessel, which flows through the material and liberates the volatile compounds. Heat may be applied, which may be in the form of warm or hot liquid, to elevate the temperature of the liquid $CO_2$ and cause at least a portion of the $CO_2$ to cross the saturation line and undergo a phase change from liquid to gas. This phase change to a gas causes a change in the pressure within the extraction vessel, which promotes extraction of the volatile compounds. The rise in temperature can be controlled, thus also controlling the pressure within the system.

The liquid $CO_2$ and the volatiles flow via gravity to a collection chamber. The temperature within the collection chamber may be increased, and the remaining liquid $CO_2$ may be boiled off, thus leaving the volatile compounds in the collection chamber. The gaseous $CO_2$ may be condensed back to a liquid and returned to a liquid storage tank for use in a later extraction process.

At block 706, non-volatile compounds may be extracted from the material. In some instances, a gentle extraction process (e.g., relatively low temperature and pressure) is used to extract the volatile compounds, which does not extract the non-volatile compounds, but rather, leaves them in tact within the material. During a subsequent process, such as at block 706, liquid $CO_2$ is introduced to the material and the temperature and pressure are raised to a desired range in order to extract the non-volatile compounds from the material. Similarly to the volatiles, the liquid $CO_2$ and the non-volatiles may flow to a collection chamber for storage. The liquid $CO_2$ in the collection chamber may be boiled off and returned to the liquid storage tank.

The process of extracting non-volatile compounds may be repeated a number of times to harvest a desirable amount of the non-volatile compounds from the material. The process parameters may be altered for one or more of the extraction processes. For example, the process may initially start at a relatively low temperature and pressure, and the temperature and pressure may be gradually increased through subsequent processes. In some cases, a modifier may be added to the solvent to influence the extraction efficacy, the solvent, or the resulting product.

At block 708, other compounds may be extracted. This may be accomplished by increasing the temperature and pressure within the extraction vessel. In some cases, the process to extract other compounds may be an SCFE process in which the $CO_2$ is heated and pressurized to a supercritical state.

At block 710, the solvent is recovered, such as by condensing the gaseous $CO_2$ and returning it to a liquid. Any remaining gaseous $CO_2$ may be vented to the atmosphere. Additionally, the extracted compounds may be recovered from the collection chambers where they can be mixed as desired to create finished products suitable for use as desired.

In some of the embodiments described herein, a closed thermodynamic system operates to perform compound extraction through a sequential series of extraction cycles. There is no need for electrical power, pneumatics, or external chillers. The liquid solvent can be used as a refrigerant, and in some cases, hot water (e.g. between about 32-55° C.) is used to phase change the liquid solvent to a gas. Thus, the materials introduced into the system are the starting material, and liquid $CO_2$. There is little loss from the system, which can extract compounds through sequential extraction processes without further external input or reloading of solvent.

Although the subject matter has been described in language specific to structural features and/or methodological acts, it is to be understood that the subject matter defined in the appended claims is not necessarily limited to the specific features or structure described. Rather, the specific features and structure are disclosed as exemplary forms of implementing the claims.

We claim:

1. A method of extracting *Cannabis* botanicals, comprising:
    passing sub-critical liquid carbon dioxide through a *Cannabis* plant to thereby extract one or more terpenes or one or more cannabinoids from the *Cannabis* plant;
    collecting the one or more terpenes or the one or more cannabinoids in a first collection chamber;
    passing super-critical liquid carbon dioxide through the *Cannabis* plant to thereby extract other compounds from the *Cannabis* plant; and
    collecting the other compounds in a second collection chamber separate from the first collection chamber.

2. The method of claim 1, wherein passing sub-critical liquid carbon dioxide through the *Cannabis* plant is carried out at a pressure of less than about 500 psi and a temperature of less than 0° C. and one or more terpenes are extracted from the *Cannabis* plant.

3. The method of claim 2, wherein the pressure is controlled by an addition of heat to boil at least some of the sub-critical liquid carbon dioxide.

4. The method of claim 1, wherein passing sub-critical liquid carbon dioxide through the *Cannabis* plant is carried out at a pressure of between about 500 psi to about 950 psi and at a temperature of between about 0° C. and 28° C. and one or more cannabinoids are extracted from the *Cannabis* plant.

5. The method of claim 4, wherein passing sub-critical liquid carbon dioxide through the *Cannabis* plant comprises repeatedly flashing the sub-critical liquid carbon dioxide through the *Cannabis* plant.

6. The method of claim 1, wherein passing super-critical liquid carbon dioxide through the *Cannabis* plant is carried out at a pressure above 950 psi and a temperature above 28° C.

7. The method of claim 1, further comprising:
    mixing the one or more terpenes or the one or more cannabinoids with the other compounds to form a product.

8. The method of claim 1, wherein the other compounds comprise one or more of fats, lipids, waxes, water and plant pigments.

9. The method of claim 1, further comprising:
    separating the one or more terpenes or the one or more cannabinoids from the sub-critical liquid carbon dioxide by applying hear to the first chamber to convert the sub-critical liquid carbon dioxide to a gas; and removing the gas from the first chamber.

10. The method of claim 9, further comprising:

converting the gas back to sub-critical liquid carbon dioxide; and using the converted sub-critical liquid carbon dioxide in subsequent extraction of botanicals from *Cannabis* plants.

11. A method of extracting *Cannabis* botanicals, comprising:

passing sub-critical liquid carbon dioxide through a *Cannabis* plant to thereby extract one or more terpenes or one or more cannabinoids from the *Cannabis* plant;

collecting the one or more terpenes or the one or more cannabinoids in a first collection chamber;

passing sub-critical liquid carbon dioxide through the *Cannabis* plant to thereby extract one or more cannabinoids from the *Cannabis* plant;

collecting the one or more cannabinoids in a second collection chamber separate from the first collection chamber;

passing super-critical liquid carbon dioxide through the *Cannabis* plant to thereby extract other compounds from the *Cannabis* plant; and collecting the other compounds in a third collection chamber separate from the first collection chamber and the second collection chamber.

12. The method of claim 11, wherein passing sub-critical liquid carbon dioxide through the *Cannabis* plant to thereby extract one or more terpenes is carried out at a pressure of less than about 500 psi and a temperature of less than 0° C.

13. The method of claim 12, wherein the pressure is controlled by an addition of heat to boil at least some of the sub-critical liquid carbon dioxide.

14. The method of claim 11, wherein passing sub-critical liquid carbon dioxide through the *Cannabis* plant to thereby extract one or more cannabinoids is carried out at a pressure of between about 500 psi to about 950 psi and at a temperature of between about 0° C. and 28° C.

15. The method of claim 14, wherein passing sub-critical liquid carbon dioxide through the *Cannabis* plant to thereby extract one or more cannabinoids comprises repeatedly flashing the sub-critical liquid carbon dioxide through the *Cannabis* plant.

16. The method of claim 11, wherein passing super-critical liquid carbon dioxide through the *Cannabis* plant is carried out at a pressure above 950 psi and a temperature above 28° C.

17. The method of claim 11, further comprising:

mixing the one or more terpenes with the one or more cannabinoids to form a product.

18. The method of claim 17, wherein the ratio of the one or more terpenes and the one or more cannabinoids when mixing to form the product is altered to adjust the viscosity of the product.

19. The method of claim 11, further comprising:

mixing the one or more terpenes, the one or more cannabinoids, and the other compounds to form a product.

20. The method of claim 19, wherein the other compounds comprise one or more of fats, lipids, waxes, water and plant pigments.

21. The method of claim 17, wherein the sub-critical liquid carbon dioxide is separated from the one or more terpenes and the one or more cannabinoids prior to mixing the one or more terpenes with the one or more cannabinoids.

22. A method of extracting *Cannabis* botanicals comprising:

passing sub-critical liquid carbon dioxide through a *Cannabis* plant to thereby extract one or more terpenes or one or more cannabinoids from the *Cannabis* plant;

collecting the one or more terpenes or the one or more cannabinoids in a first collection chamber;

passing super-critical liquid carbon dioxide through the *Cannabis* plant to thereby extract other compounds from the *Cannabis* plant;

collecting the other compounds in a second collection chamber separate from the first collection chamber; and recovering one or more of the terpenes, cannabinoids, or other compounds.

* * * * *